（12）United States Patent
Schrörs et al.

(10) Patent No.: US 11,285,253 B2
(45) Date of Patent: Mar. 29, 2022

(54) BLOOD TREATMENT APPARATUS AND ORGANIZER

(71) Applicant: Fresenius Medical Care Deutschland GmbH, Bad Homburg (DE)

(72) Inventors: Alexander Schrörs, Frankfurt am Main (DE); Jürgen Klewinghaus, Oberursel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 791 days.

(21) Appl. No.: 16/070,996

(22) PCT Filed: Jan. 17, 2017

(86) PCT No.: PCT/EP2017/050875
§ 371 (c)(1),
(2) Date: Jul. 18, 2018

(87) PCT Pub. No.: WO2017/125382
PCT Pub. Date: Jul. 27, 2017

(65) Prior Publication Data
US 2019/0022299 A1    Jan. 24, 2019

(30) Foreign Application Priority Data
Jan. 20, 2016 (DE) .................... 102016100934.2

(51) Int. Cl.
*A61M 1/36* (2006.01)
*A61M 1/16* (2006.01)
*A61M 1/34* (2006.01)

(52) U.S. Cl.
CPC ........ *A61M 1/3653* (2013.01); *A61M 1/1621* (2014.02); *A61M 1/3621* (2013.01);
(Continued)

(58) Field of Classification Search
CPC .......... A61M 2205/121; A61M 1/3653; A61M 1/1621; A61M 2205/14; A61M 2209/08
See application file for complete search history.

(56) References Cited

U.S. PATENT DOCUMENTS 5,752,813 A * 5/1998 Tyner .................. F04B 43/1253
417/477.2
9,081,382 B2   7/2015 Doyle et al.
(Continued)

FOREIGN PATENT DOCUMENTS

CN     102056636      5/2011
CN     102215942      10/2011
(Continued)

OTHER PUBLICATIONS

International Search Report and Written Opinion in International Application No. PCT/EP2017/050875, dated Mar. 21, 2017, 9 pages (English Translation).
(Continued)

*Primary Examiner* — Leslie R Deak
(74) *Attorney, Agent, or Firm* — Fish & Richardson P.C.

(57) ABSTRACT

The present disclosure relates to a blood treatment apparatus having of each at least one control device; one user interface; one receiving section for releasably receiving an organizer, wherein the organizer comprises components releasably connected thereto for the extracorporeal blood treatment options, in particular dialysis method being executable by the blood treatment apparatus, wherein the blood treatment apparatus comprises in particular in the area of its reception section or in the area corresponding thereto a device for the releasable fastening or fixing of the organizer (on)to the blood treatment apparatus and/or at least a device for acting (Continued)

on components of an organizer which is releasably received in or on the receiving section. Furthermore, an organizer is specified.

12 Claims, 5 Drawing Sheets

(52) U.S. Cl.
CPC ............... *A61M 1/16* (2013.01); *A61M 1/34* (2013.01); *A61M 1/3413* (2013.01); *A61M 1/3496* (2013.01); *A61M 2205/121* (2013.01); *A61M 2205/14* (2013.01); *A61M 2205/502* (2013.01); *A61M 2205/6018* (2013.01); *A61M 2209/08* (2013.01)

(56) References Cited

U.S. PATENT DOCUMENTS

| | | |
|---|---|---|
| 9,801,991 B2 | 10/2017 | Rada |
| 2005/0070837 A1 | 3/2005 | Ferrarini et al. |
| 2009/0084717 A1 | 4/2009 | Delmage et al. |
| 2010/0121246 A1 | 5/2010 | Peters et al. |
| 2011/0139652 A1 | 6/2011 | Klewinghaus et al. |
| 2012/0075266 A1 | 3/2012 | Shimizu et al. |
| 2013/0165847 A1 | 6/2013 | Scarpaci et al. |
| 2014/0112828 A1* | 4/2014 | Grant ................ A61M 1/1658 422/44 |
| 2014/0178215 A1* | 6/2014 | Baxter ............... A61F 9/00736 417/360 |
| 2015/0314055 A1 | 11/2015 | Hogard et al. |

FOREIGN PATENT DOCUMENTS

| | | |
|---|---|---|
| CN | 104321087 A | 1/2015 |
| CN | 104870033 | 8/2015 |
| CN | 105142690 A | 12/2015 |
| DE | 102012000410 | 7/2013 |
| WO | WO 2009/146913 | 12/2009 |

OTHER PUBLICATIONS

International Preliminary Report on Patentability in International Application No. PCT/EP2017/050875, dated Jul. 24, 2018, 7 pages (English Translation).

* cited by examiner

BLOOD TREATMENT APPARATUS AND ORGANIZER

CROSS-REFERENCE TO RELATED APPLICATIONS

The present application is a national stage entry of International Patent Application No. PCT/EP2017/050875, filed on Jan. 17, 2017, which claims priority to Application No. DE 10 2016 100 934.2, filed in the Federal Republic of Germany on Jan. 20, 2016. The disclosure of the prior applications are expressly incorporated herein by reference thereto.

TECHNICAL FIELD

This disclosure relates to a blood treatment apparatus and an organizer.

BACKGROUND

Apparatuses for the extracorporeal blood treatment, in particular for the dialysis treatment, are known from practice. Different treatment methods or treatment options may optionally be executed by means of said apparatuses. A different number or amount of blood tubing sets (disposables) and associated blood tubing set components, e.g. tubing connections and the like is thereby required for different treatment options, respectively.

Assembling blood set components for forming blood tubes is known in the state of the art, from which blood tubes resp. treatment sets may be assembled for different treatment options. Such assemblies, as known e.g. from WO 2009/146913 A2, may be clearly and suitably provided on so-called organizers or trays for the coupling of the utilized blood treatment apparatus. Depending on the treatment option to be executed, the blood tubing set components required thereto may be connected correspondingly. The blood tubing set components, which are not needed for the selected treatment option, remain unused on the organizer.

One disadvantage associated thereto is that the plurality of blood tubing set components provided on the organizer and the diverse possibilities as to how to connect them to each other may confuse the clinic personnel, hence, leading often and in particular under time pressure to an incorrect selection and connecting or connection of blood tubing set components. In addition, preparing a ready-to-use blood tubing set—for the selected treatment option—from the blood tubing set components provided on the organizer requires experience and is moreover time-consuming since several tubing sets or tubing lines must often be traced or observed precisely in order to avoid an incorrect connection and confusions or mistakes, and at the same time an overview of a large number of similarly looking blood tubing set components must be kept or maintained in mind.

This disclosure describes a further organizer which comprises, holds or carries components, in particular blood tubing set components, for the blood treatment. Furthermore, a blood treatment apparatus, which comprises the organizer or is prepared thereto, is specified herein.

Thus, a blood treatment apparatus, which comprises at least, of each, one control device, one user interface and one receiving section, is described herein.

SUMMARY

The receiving section serves the releasable reception of an organizer, which comprises components, in particular blood tubing set components, releasably connected to it. Some or all of these components are designed or designated or set for an extracorporeal blood treatment method, which is executable by the blood treatment apparatus.

The blood treatment apparatus comprises at least a device for acting on components of an organizer, which is releasably received in the receiving section. This device is preferably in the area of the receiving section or in the area corresponding to it.

The blood treatment apparatus optionally further comprises at least one device for the releasable fastening of the organizer thereon, in particular on the receiving section.

An organizer with at least one fastening device arranged thereto is further proposed, by means of which fastening device at least one component, in particular a blood tubing set component, is releasably held or kept to or at a further section of the organizer, e.g. to or at a rear thereof.

The further section and/or the fastening device may optionally comprise an opening through which a device for acting on components may be brought into contact with the component and/or with the fastening device, e.g. through sections of the fastening device.

The fastening device may optionally be connected by a releasable adhesive to a further section of the organizer, e.g. its rear.

The fastening device may optionally comprise a connector, which is connectable, or embodied for same, to a device for acting on components of the blood treatment apparatus.

The fastening device and/or a component releasably received in the organizer may optionally comprise a magnetic element.

Embodiments may encompass one or several of the aforementioned or following features in any combination, unless the person skilled in the art recognizes their combination as technically impossible. Embodiments are furthermore subject matter of the dependent claims.

In all the statements made herein, the use of the expression "may be" or "may have" and so on, is to be understood synonymously with "preferably is" or "preferably has," and so on respectively, and is intended to illustrate an embodiment. Whenever numerical words are mentioned herein, the person skilled in the art shall recognize or understand them as indications of numerical lower limits. Unless it leads the person skilled in the art to an evident contradiction, the person skilled in the art shall comprehend the specification for example of "one" encompassing also "at least one". This understanding is also equally encompassed in certain aspects, as the interpretation that a numeric word, for example, "one" may alternatively mean "exactly one", wherever this is evidently technically possible for the person skilled in the art. Both apply herein to all used numerical words.

Spatial indications made herein as "top", "bottom" and so on refer in case of doubt to the illustration as depicted in the accompanying figures.

In certain exemplary embodiments, speaking of a component may also be understood as a combination of components, in particular connected components.

In certain exemplary embodiments, the organizer is used for releasably receiving and/or releasably fixing components of blood tubes for different extracorporeal blood treatment options, in particular in dialysis procedures, with a blood treatment apparatus such as, for example, a dialysis apparatus. Suitable devices for releasably receiving and/or fixing such components to the organizer are provided at or on the organizer.

In certain exemplary embodiments, the organizer comprises a one-piece main body. The latter can carry or comprise the devices for the releasable reception and/or releasable fixing.

In certain exemplary embodiments, the organizer is made of, or comprises, polystyrene.

In certain exemplary embodiments, the organizer is produced, inter alia, by thermoforming.

In certain exemplary embodiments, the user interface may be or may comprise an input device and/or an output device. The output device may be a display, a monitor or a screen. An input device may be a keyboard, a touch screen or the like.

The control device may be configured or programmed to display one or several components of the organizer and/or an equipping manual or an instruction for equipping the components to or at the blood treatment apparatus.

In certain exemplary embodiments, the device for acting on components is embodied or arranged in order not to act directly on a component but on a fastening device of the organizer by means of which fastening device the respective component is releasably held to or at the organizer, e.g. at a rear thereof. Therefore, the "device for acting on components" is to be understood in certain exemplary embodiments also as a device, which acts on the fastening device, which releasably holds the component on the organizer.

In certain exemplary embodiments, a component is a blood tubing set component. The present invention is however not to be limited thereto. When a component is mentioned herein, this may also undimishedly apply to a blood tubing set component and vice versa.

In certain exemplary embodiments, the device for acting on components of the organizer is, or comprises, a device for releasing components of the organizer, a device for actively separating components from the organizer and/or a device for holding components on or to the organizer.

"Releasing" is understood in certain exemplary embodiments in the sense that the (released) component may, starting from the moment of the release (but not before), be manually removed from the organizer by the user in the usual manner (i.e. for example. without being or having to be destructive or without using tools). "Releasing" may allow detaching passively.

"Separating" is understood in certain exemplary embodiments in the sense that the separated component may, starting from the moment of the separation (but not before), not be manually released from the organizer by the user because it is already not connected to the organizer anymore. "Separating" may, like "ejecting", also be an active release.

"Holding" is understood in certain exemplary embodiments in the sense that the held component, may, until the moment in which the holding is terminated, not be manually removed from the organizer by the user in the usual manner (i.e. for example, not without being destructive or without using tools). The component may be manually removed only after termination of the holding state.

In certain exemplary embodiments, the device for acting on components of the organizer is embodied as, or comprises, at least a mechanically acting element.

Examples of a mechanically-acting element encompass devices for ejecting the component, devices for releasing a bar of the organizer, rotating devices for unlocking a Bayonet lock or a lug of the organizer, devices for opening an undercut or a back cut of the organizer and/or devices for spreading apart or clamping two sections of the organizer, wherein the latter being arranged to act in particular on the side of the organizer received in the receiving section, facing the receiving section or the blood treatment apparatus.

In certain exemplary embodiments, the device for acting on components of the organizer is embodied as, or comprises, an energy source or an emitter for emitting waves, light and/or heat, and/or a magnetic source.

In certain exemplary embodiments, the control device is configured and/or programmed to activate or control the device for acting on components such that said device acts on at least one component held by the organizer, which is releasably received in the receiving section.

In certain exemplary embodiments, the control device is configured and/or programmed to act on components of the organizer depending on a component illustrated or designated by the user interface. "Acting on" is achieved by a device for acting on components. "Depending on" may refer, in certain exemplary embodiments, to the order or sequence with which the components are illustrated or designated by the user interface.

This means that in such embodiments the components are acted on "in the same order" in which they are displayed or designated by the user interface, e.g. on the screen. If the user interface for example initially shows on a screen (e.g. when reading an instruction for equipping the components onto the blood treatment apparatus) a first then a second and finally a third component, then initially the first component, then the second, and finally the third are acted on.

In this way, for example, components of the organizer may be released or ejected in a defined or determined order, which corresponds to the order in which the released or ejected components are displayed for the user on the user interface, for example when reading the instruction for equipping the blood treatment apparatus. A programming be exemplarily mentioned herein by which the user is instructed on a certain page of the instructions for equipping, to place or insert the alpha chip of the blood pump on the blood treatment apparatus and the alpha chip is accepted or rejected by the control device for its use by the user. If the user further virtually scrolls down in the instructions for equipping on the user interface and if he is requested on a later page to equip a next component, then this next component is released or ejected for him by the control device, for example concurrently to showing him the next component on the screen.

In some exemplary embodiments, the control device is programmed to act, e.g. through releasing or ejecting, exactly on this specific component of the organizer when it is being displayed on the user interface.

Such an embodiment may be referred to as a pure user-interface controlling.

Such an embodiment is of course not to be limited to a first and to a second component, rather it may refer to any component or to an order of components provided on the organizer. This applies optionally generally whenever "first" and "second" components are mentioned herein.

In certain exemplary embodiments, the blood treatment apparatus comprises, or is connected in signal communication to, a detection device, which itself is in signal communication with the control device. The detection device is configured to detect a connection of the pre-determined first component to the blood treatment apparatus, i.e. to determine that, or whether, a first component is connected to the blood treatment apparatus.

In certain exemplary embodiments, the control device is configured and/or programmed, when detecting an established connection of the first pre-determined component (i.e. when it detects that a connection between the first component and the blood treatment apparatus has been established), to act on a pre-determined second component by means of the device for acting on components. "Acting on" may be a release or releasing. Alternatively, the control device is configured and/or programmed in some exemplary embodiments to act on a pre-determined second component, again by the device for acting on components, until an established connection of the first pre-determined component has been detected by the detection device ("until" means until the latter detects that a connection between the first component and the blood treatment apparatus has been established or achieved). Here, "acting on" may be holding.

In this way, for example components may always be then released or ejected when it has been detected that a preceding component (the order in which the components to be connected may be kept accessible saved for the control device) has been connected to the blood treatment apparatus. For example, if the citrate pump clip is inserted into the citrate drip chamber, then this leads to ejecting the citrate line from the organizer.

Such an embodiment may be referred to as pure event control.

In certain exemplary embodiments, the control device is configured and/or programmed to request from the user by the user interface to connect the blood treatment apparatus to a pre-determined component of the organizer. To make sure that the user has connected the specific or precise component to the blood treatment apparatus, corresponding signals of a detection device are awaited, evaluated or assessed.

In these embodiments, the user is requested by the user interface to connect the blood treatment apparatus to a pre-determined further component of the organizer, once or when a completed connection of the first pre-determined component or a completed removal of the first pre-determined component from the organizer has been detected by the detection device. In this way, the device for acting on components acts on the pre-determined further component of the organizer. "Acting on" may be releasing. Alternatively, the control device is configured and/or programmed in some exemplary embodiments to act on a pre-determined second component, and namely by the device for acting on components, until a completed connection of the first pre-determined component or a completed removal of the first pre-determined component has been detected by the detection device ("until" means until it detects that a connection between the first component and the blood treatment apparatus has been established or achieved). Here, "acting on" may be holding.

In this way, for example components may always be then released or ejected when it has been detected that a preceding component (the order in which the components to be connected may be maintained or kept accessible or saved for the control device), for which connection the user has been requested in a previous step, has in fact been connected to the blood treatment apparatus. In connection therewith, an automatic, virtual scrolling within the instructions for equipping may be accompanied by a corresponding illustration on the user interface.

Such an embodiment may also be referred to as a combination of user interface control and event control.

In certain exemplary embodiments, the blood treatment apparatus comprises at least a detection device, which is in signal communication with the control device. The detection device is configured to detect a connection of a device required for the blood treatment, which device being not necessarily a component of the organizer, to the blood treatment apparatus. Alternatively or additionally, the detection device is configured to detect that a pre-determined activity or process required for executing a blood treatment, e.g. the T1-test, a pressure retention or maintenance test or the like is completed.

The control device in these embodiments is configured and/or programmed to evaluate signals of the detection device with respect to the established connection of the device or the completed activity/completed process. The control device in these embodiments is further configured and/or programmed to act on a pre-determined component of the organizer by the device for acting on components of the organizer when it detects that the connection of the device or the activity or the process has been completed. Here, "acting on" may be a release. Alternatively, the control device is configured and/or programmed in some exemplary embodiments to act on a pre-determined component, and namely by the device for acting on components, until the completion of the connection or the activity/the process has been detected by the detection device. Here, "acting on" may be holding.

In certain exemplary embodiments, the blood treatment apparatus is releasably connected to an organizer which itself holds components releasably connected to it.

In certain exemplary embodiments, the blood treatment apparatus is a hemodialysis apparatus, a hemodiafiltration apparatus, a hemofiltration apparatus and/or an apheresis apparatus.

Some or all of the embodiments may encompass one or several of the aforementioned or the following advantages.

One advantage is that when "acting on" is in the sense of holding, then an early connection of certain components to the blood treatment apparatus by the user may be prevented. This may prevent that components which are not required for checking the blood treatment apparatus, e.g. with respect to the so-called T1-test, which however may affect or disturb this test, are not connected prior to completing this T1test. This may be achieved by holding the component, thus preventing its removal from the organizer and its subsequent connection.

Holding may further advantageously ensure that a surplus of components of the organizer, i.e. components, which are not required for an envisaged blood treatment option, cannot be removed from the organizer until the completion of the equipping of the blood treatment apparatus or longer. In this way, a surplus of components is not unintentionally equipped.

Moreover, the user is advantageously supported with respect to the order in which the components available on the organizer are to be connected to the blood treatment apparatus; the control device releases the components in the correct order, if desired. That the individual components thereby tangle, overlap or intersect may be additionally excluded through their clever arrangement on the organizer in advance, moreover, by holding and/or by releasing/ejecting them in the pre-determined, optimized order. The precise or intended release/ejection or holding may further offer an advantage, since the user has always to observe and connect only single or individual components; the control device instructs him which component this is at the respective or relevant point of time. This serves for clarity (or the clear view) by which the high number of components is made controllable for the user.

In particular, by actively ejecting the components, the effort needed by the user to release the component from the organizer may be maintained low.

BRIEF DESCRIPTION OF THE FIGURES

The present invention shall be exemplarily explained with regard to the accompanying drawings in which identical reference numerals refer to the same or similar components. The following applies in the partly highly simplified figures.

DETAILED DESCRIPTION

Figure 1:
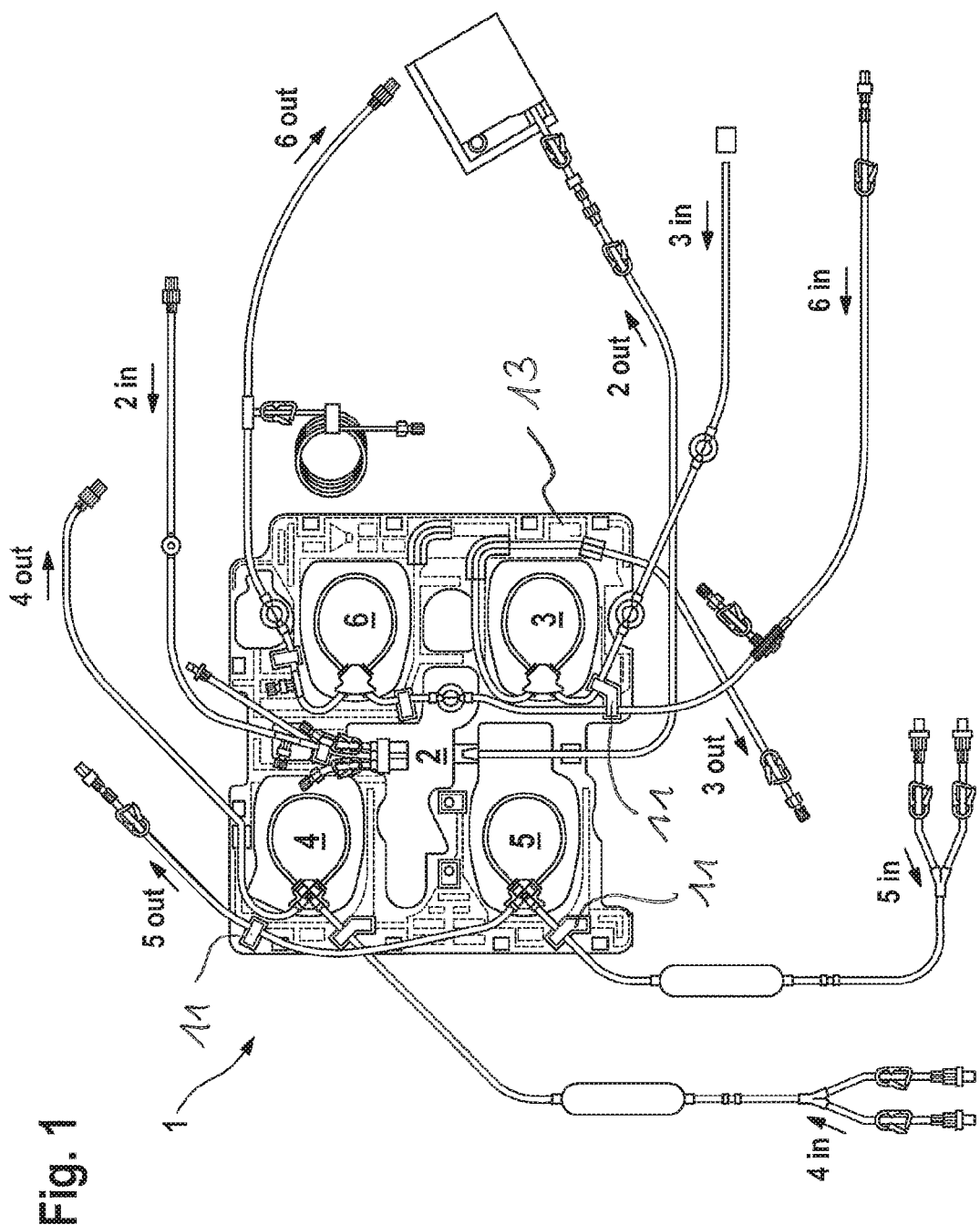
FIG. 1 shows a top view of an exemplary organizer.

FIG. 1 shows, schematically simplified, an exemplary equipped organizer 1 (referred to also as tray), which is equipped with a return line 2 for returning blood from a filter, not shown, to the patient, a filtrate line 3 from the filter to a filtrate bag, not shown, a dialysate line 4 for dialysis fluid or exchange fluid or replacement fluid from a solution bag, not shown, to the filter or connecting piece, a substituate line 5 for exchange fluid from the solution bag to the connecting piece and an access line 6 from the patient to the filter or to the return line 2.

Thereby, the return line 2 comprises a filter connector 2in and a patient connector 2out with a rinsing bag. The filtrate line 3 comprises a filter connector 3in and a connector 3out for the filtrate bag. The dialysate line 4 comprises a connector 4in for the solution bag and a filter connector 4out for a connecting piece in the access line or return line. The substituate line 5 comprises a connector 5in for the solution bag and a connector 5out for the connecting piece in the access or return line. The access line 6 from the patient to the filter comprises a patient connector 6in and a filter connector 6out.

The aforementioned elements with reference numbers 2 to 6 represent blood tubing or blood tubing set components and are examples of components, which may be releasably connected to an organizer 1.

The organizer 1 comprises fastening devices 11 which serve the releasable connection of the blood tubing set-components to a rear 13 (usually made of a more or less stiff material) or to another section of the organizer 1.

Figure 3:
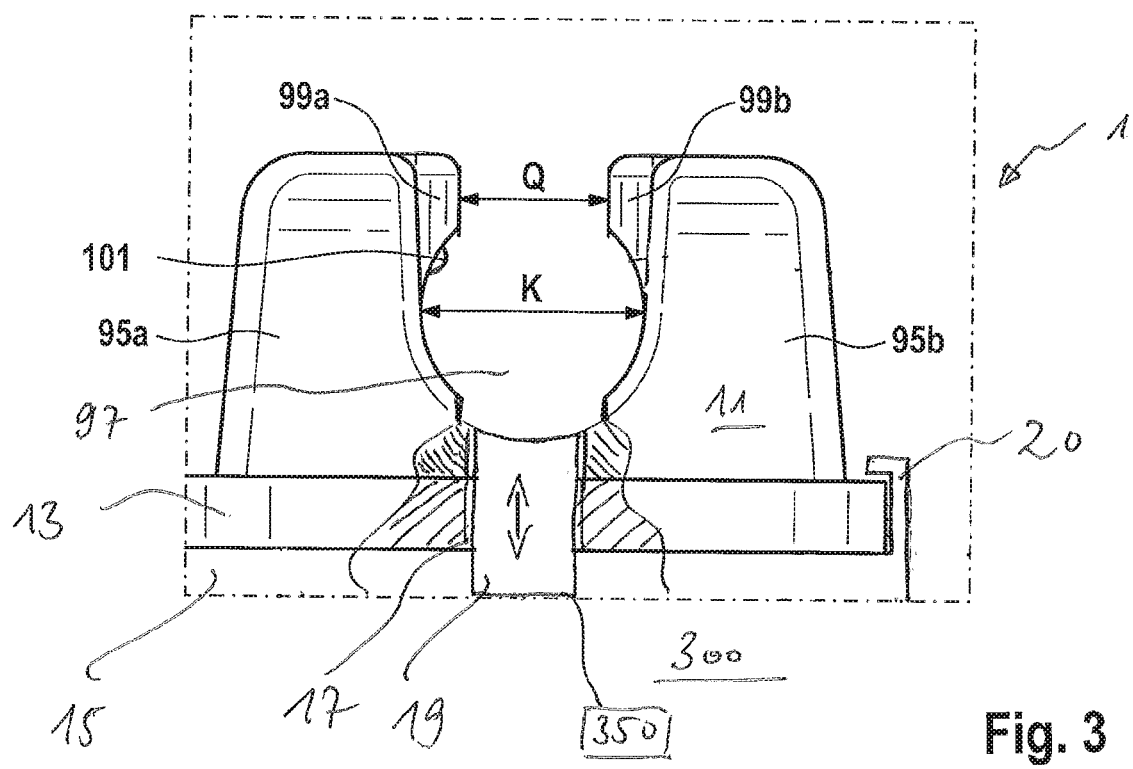
FIG. 3 shows a fastening device of the organizer with respect to a first embodiment in a front view, without blood tubing set components.

It is not seen in FIG. 1 that several fastening devices 11 comprise openings as shown in FIG. 3 (opening 17) that optionally protrude through both the rear 13 and through sections of the fastening device 11.

Figure 2:
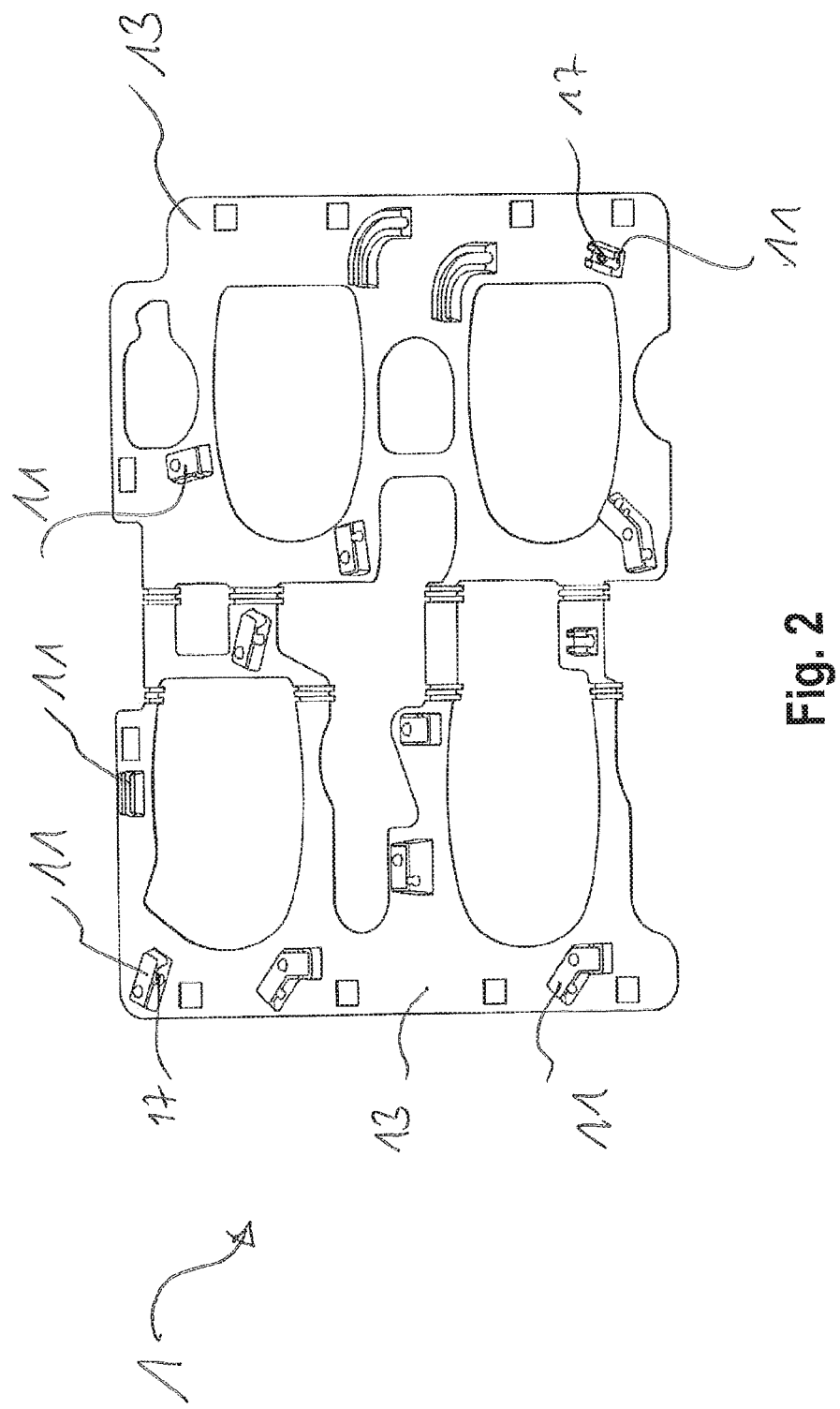
FIG. 2 shows the organizer of FIG. 1 not equipped with blood tubing set components, unlike in FIG. 1.

FIG. 2 shows a top view of the organizer 1 of FIG. 1. The organizer 1 in FIG. 2 is not equipped with blood tubing set components.

The openings 17 indicated in FIG. 2 are explained with respect to FIG. 3.

FIG. 3 shows a fastening device 11 of the organizer 1 with respect to a first embodiment in a front view. The fastening device 11 has no blood tubing set component.

The fastening device 11 is designed as a clip. It comprises two legs or arms 95a and 95b, which, respectively, laterally limit a channel 97. The channel 97 is open at the top and at its end sides (FIG. 3). This partially open or half-open designed channel 97 receives a blood tubing set component not shown in FIG. 3.

The legs 95a and 95b have each a protrusion resp. a support or reinforcement 99a or 99b pointing towards the upper opening with the width Q of the channel 97. A clamping effect on the blood tubing set component (not shown in FIG. 3) inserted into the fastening device 11 may be achieved by the reinforcements or supports 99a and 99b.

The width Q of the opening, which is less than a width K of the channel 97, in which the blood tubing set component is arranged within the fastening device 11, offers greater safety in that the blood tubing set component is not unintentionally released from the fastening device 11.

Below the channel 97, the stiff rear 13 of the organizer 1 is illustrated partially cut. One sees that the stiff rear 13 comprises an opening 17 below the channel 97 which opening 17 extends also through sections of the fastening device 11 which sections contact the rear 13.

It is further seen that the stiff rear 13 of the organizer 1 contacts a receiving section 15 of a blood treatment apparatus 300. The receiving section 15 serves for receiving the organizer 1 at the blood treatment apparatus 300 and comprises an ejector 19 in the exemplary embodiment of FIG. 3. The ejector 19 is an exemplary embodiment of the device for acting on components of an organizer 1 being releasably received in the receiving section.

The ejector 19 is arranged such that it can be moved or shifted along the direction of the double arrow of FIG. 3. When it is, with respect to FIG. 3, moved to the top, then it presses on or against the blood tubing set component, not shown in FIG. 3, extending through the channel 97 and forces the blood tubing set component in this way upwards through the opening with width Q to the top. In this way, the ejector 19 actively separates or releases the non-shown blood tubing set component from the organizer 1, hence ejects it.

The ejector 19 is in signal communication with a control device 350 of the blood treatment apparatus 300 and may be activated by it for ejecting.

It is recognizable for the person skilled in the art that there is no need for an opening 17 in the sense of a through opening, through which the ejector 19 (or the device for acting on in general) is inserted. The ejector 19 may actually also press through the closed rear 13 and in this way eject. The rear 13 may comprise a thinner section, relative to the adjacent sections of the rear 13, through which the component may be acted on by means of ejector 19 by applying only a comparatively little force.

The reference numeral 20 denotes a device for the releasable fixing of the organizer 1, e.g. by its rear 13, to the blood treatment apparatus 300, herein exemplarily at the receiving section 15. The device 20 may be understood as a support by means of which the fastening device 11 may be held relative to the device for acting on. It may further be used to prevent an evasive, deflecting or compensating movement of the organizer 1 while acting, e.g. by the ejector 19, on the fastening device.

The reference numeral 101 refers to an optional detection device which is embodied as e.g. pressure sensor, optical sensor or the like. The detection device 101 may be provided and connected to the control device 350. Its feedback may provide an indication or allow a statement as to whether the respective component has already been removed from the fastening device 11 of the organizer 1. Such indication or statement may be a prerequisite for further components to be released or ejected. The control device 350 may be programmed accordingly.

Figure 4:
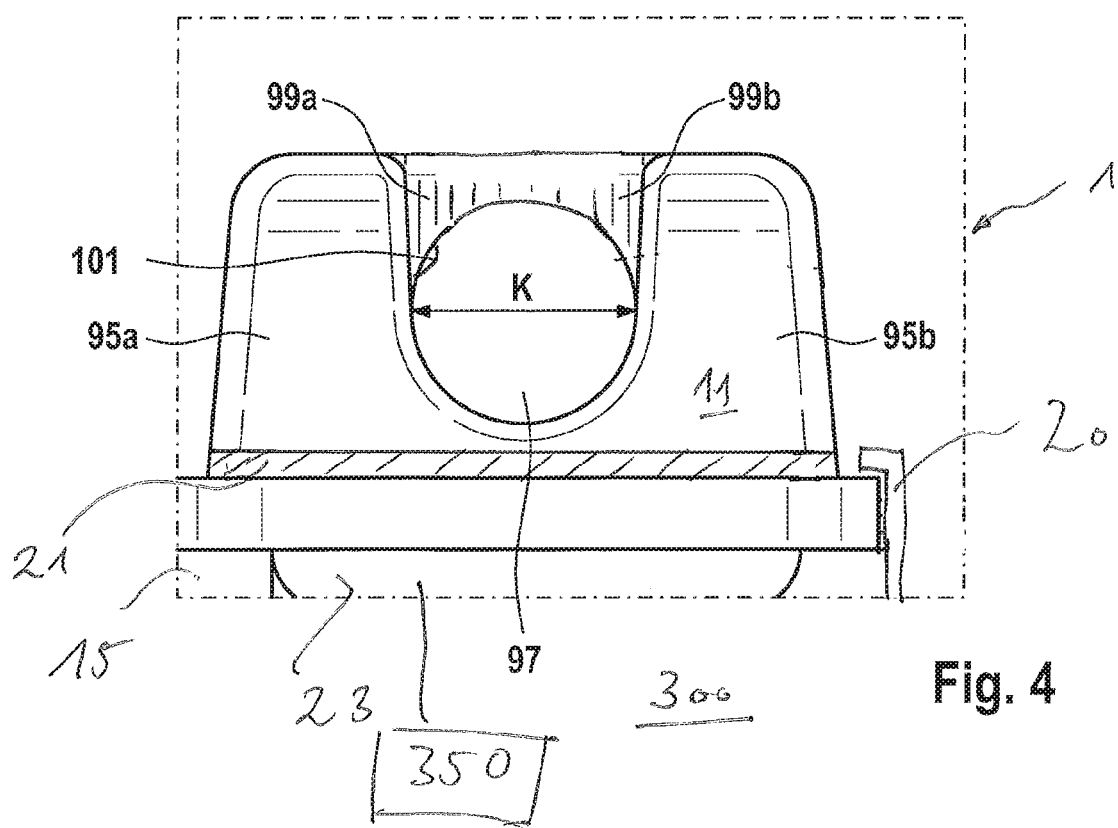
FIG. 4 shows a fastening device of the organizer with respect to a second embodiment in a front view, without blood tubing set components.

FIG. 4 shows a fastening device 11 of the organizer 1 with respect to a second embodiment in front view and again without a blood tubing set component.

Unlike in the embodiment of FIG. 3, the channel 97 is optionally not open at the top with an opening having the width Q (compare FIG. 3; nevertheless, the embodiment of FIG. 4 may also comprise such an opening). The channel 97 comprises—unlike in FIG. 3—optionally no opening for inserting an ejector 19 (compare FIG. 3) either. The channel 97 may have one or both of these openings; it may alternatively however also be closed along its circumference, as shown in FIG. 4.

Unlike the exemplary embodiment of FIG. 3, the blood treatment apparatus 300 comprises optionally no ejector 19.

The fastening device 11 of FIG. 4 is connected to the stiff rear 13 or elsewhere to the organizer 1 by an adhesive layer 21 shown in sectional view or cut. The adhesive layer 21 may include or consist of a removable adhesive or gluing material, e.g. removable by heat or UV-light.

The blood treatment apparatus 300 comprises a light or heat radiator 23, which may be part of the receiving section 15. The light or heat radiator 23 may be a UV-radiator. The radiation emitted by it allows the adhesive layer 21 to dissolve such that the fastening device 11 is detached from the rear 13.

In the example of FIG. 4, the fastening device 11 detached from the rear 13 remains completely or as a whole on the blood tubing set component. The blood tubing set component held in the fastening device 11 remains thus connected to the fastening device 11, however not to the rear 13.

In some embodiments, only part of the fastening device 11 is connected by means of an adhesive layer 21 to the rear 13 or to other parts of the organizer 1. When the adhesive layer 21 is dissolved by the light or heat radiator 23, then only the initially sealed part of the fastening device 11 is detached. The initially sealed part may be one half of the fastening device 11. The initially sealed part may be one of the legs 95a and 95b. When one of the legs 95a and 95b is detached due to applying the light or heat radiator 23, then the fastening device 11 may partially detach from the rear 13 and in this way release the blood tubing set component.

Figures 5, 6:
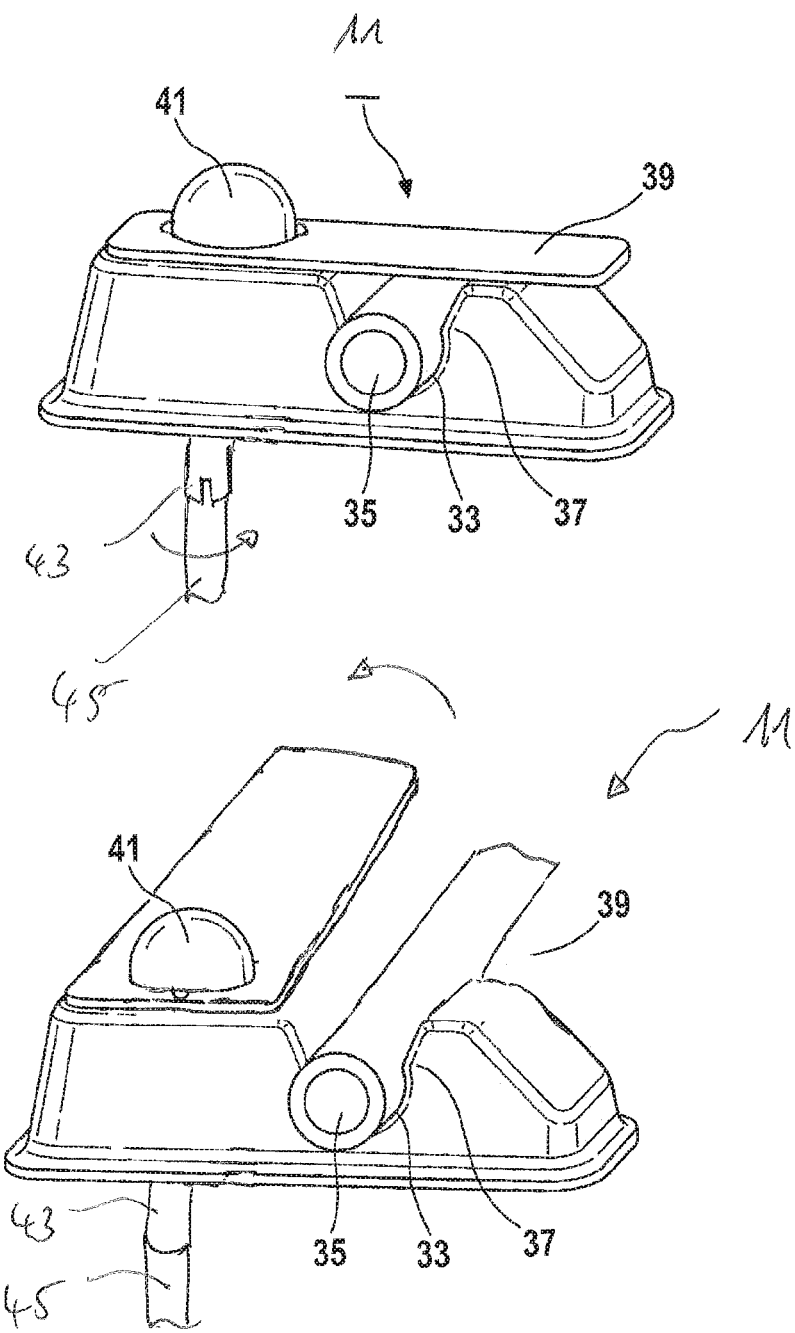
FIG. 5 shows a fastening device of the organizer with respect to a third embodiment in a front, perspective view, with blood tubing set components, in a holding state.
FIG. 6 shows the fastening device of FIG. 5 in a releasing state.

FIG. 5 shows a fastening device 11 of the organizer 1 with respect to a third embodiment in perspective view from the front and with a blood tubing set component 35.

The fastening device 11 comprises a receiving section 33 for releasably receiving a section of the blood tubing set component 35, wherein the receiving section 33 optionally comprises inclined areas 37 for a simpler reception of the blood tubing set component 35 into the receiving section 33.

In FIG. 5, a lug 39 is further shown which is fixed to the fastening device 11 by a fixing device 41. The lug 39 is, as seen when compared to FIG. 6, rotatably fixed to the fastening device 11 by the fixing device 41.

The lug 39 prevents, due to its arrangement above the blood tubing set component 35 and above the outlet opening through which the component may exit from the channel 97, an undesired release of the blood tubing set component 35 from the receiving section 33. The lug 39 can be rotated—as shown in FIG. 6—about an axis of the fixing device 41 for the desired release of the blood tubing set component 35.

The fixing device 41 is connected in a rotation-free or torque-proof manner to both the lug 39 and to an optional connector 43, which is connectable to a device 45 for the release of components. If the device 45 for the release of components rotates the connector 43 prompted by the control device 350, then the connector 43 rotates the lug 39 sideward to the side and allows the release of the blood tubing set component 35. This state is shown in FIG. 6.

FIG. 6 shows the fastening device 11 of FIG. 5 with a lug 39 opened by a device for acting on the component. Unlike in the closed state of the fastening device 11 shown in FIG. 5, the blood tubing set component 35 may be manually removed from the fastening device 11 or by an optional ejector 19, which is again not shown in FIGS. 5 and 6.

Figure 7:
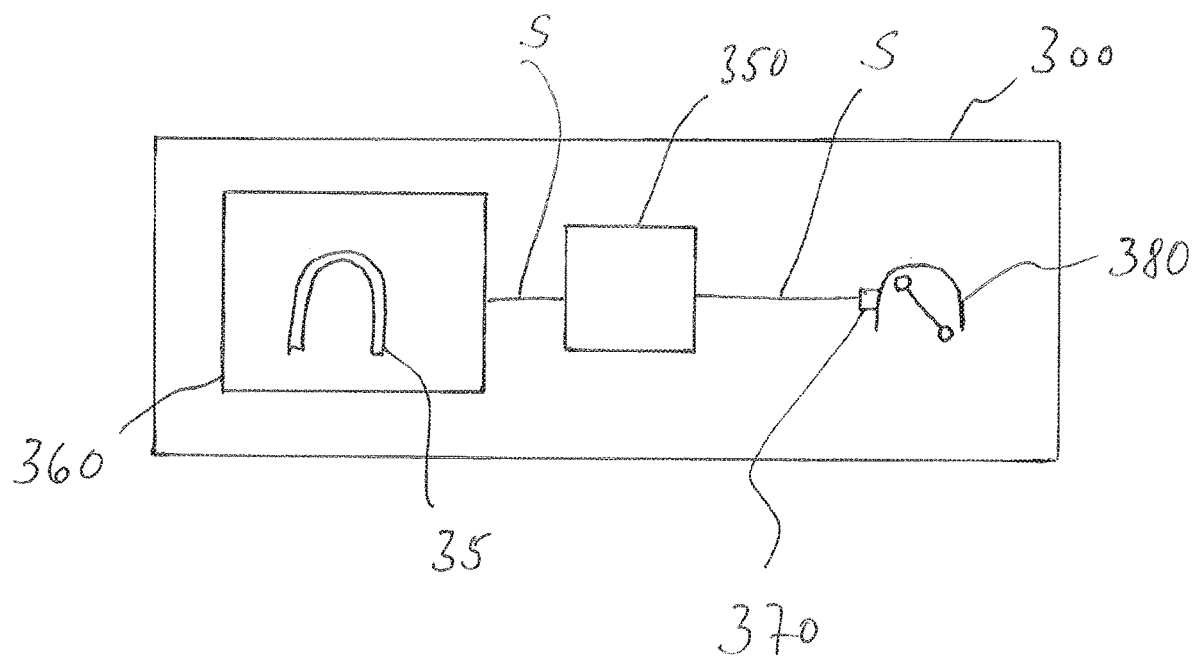
FIG. 7 shows, schematically simplified, a blood treatment apparatus in an exemplary embodiment.

FIG. 7 shows, schematically simplified, a blood treatment apparatus 300 in an exemplary embodiment.

The blood treatment apparatus 300 comprises the control device 350, which is in signal communication S with the user interface 360 and with a detection device 370.

The user interface 360 illustrates to the user, for example during an instruction for equipping the blood treatment apparatus 300 with blood tubing set components of an organizer 1, the blood tubing set component 35 as component with which the blood treatment apparatus 300 is to be equipped next.

The detection device 370 is arranged and configured to detect that the insertion of the blood tubing set component 35 into the blood pump 380 has been completed.

Only once the control device 350 can ascertain or determine by the detection device 370 that the blood tubing set component 35 also has actually also been inserted into the blood pump 380, the user is shown by the interface 360 which component (not shown) is to be connected next. The latter may be released or ejected after detecting that the blood tubing set component 35 has been connected and/or after the next component has been shown on or at the user interface 360.

LIST OF REFERENCE NUMERALS

1 organizer
2 return line, component
3 filtrate line, component
4 dialysate line, component
5 substituate line, component
6 access line, component
2in filter connector, component
2out patient connector, component
3in filter connector, component
3out connector, component
4in connector, component
4out filter connector, component
5in connector, component
5out connector, component
6in patient connector, component
6out filter connector, component
11 fastening devices
13 rear
15 receiving section
17 opening
19 ejector, device for ejecting; device for actively separating components
20 device for releasably fastening or fixing the organizer on the receiving section
21 adhesive layer
23 light or heat radiator, power source or emitter for emitting waves, light and/or heat
33 receiving section
35 blood tubing set component, component, pre-determined first component, illustrated or designated component 37 areas
39 lug
41 fixing device
43 connector
45 device for releasing components
95a leg or arm
95b leg or arm
97 channel
99a protrusion
99b protrusion
101 detection device
300 blood treatment device
350 control or regulating device
360 user interface
370 detection device
380 blood pump
K width of the channel 97
Q width of the opening of channel 97
S signal communication

The invention claimed is:

1. A blood treatment apparatus, comprising:
a control device;
a user interface; and
a receiving section for releasably receiving an organizer that is releasably connected to multiple components of a blood tubing set used for performing extracorporeal blood treatment options executable by the blood treatment apparatus,
wherein the receiving section of the blood treatment apparatus comprises: a) a device for releasably fastening the organizer to the blood treatment apparatus, and b) multiple devices for acting on the multiple components of the blood tubing set of an organizer releasably received by the receiving section, wherein the multiple devices of the receiving section comprise one or more of:
a device for releasing the multiple components of the blood tubing set from being connected to the organizer for their manual removal from the organizer,
a device for actively separating the multiple components of the blood tubing set from the organizer, and
a device for holding the multiple components of the blood tubing set on the organizer, and
wherein each device of the multiple devices of the receiving section acts on a respective individual component of the multiple components of the blood tubing set.

2. The blood treatment apparatus according to claim 1, wherein the multiple devices of the receiving section comprises:
a mechanically operating element comprising at least one of:
a device for ejecting,
a device for opening a lock or bar of the organizer,
a rotating device for unlocking a Bayonet lock or a lug of the organizer,
a device for opening an undercut or a back cut of the organizer, and
a device for spreading apart, strutting, bridging, or clamping two sections of the organizer.

3. The blood treatment apparatus according to claim 1, wherein the multiple devices of the receiving section comprises:
an energy source or energy emitter for emitting waves, light, or heat, or
a magnetic field source.

4. The blood treatment apparatus according to claim 1, wherein the control device is configured to individually activate each device of the multiple devices of the receiving section in order to individually act on each respective individual component of the multiple components of the blood tubing set.

5. The blood treatment apparatus according to claim 1, wherein the control device is configured to act on components of the organizer illustrated or designed by the user interface, by activating one or more of the multiple devices of the receiving section.

6. The blood treatment apparatus according to claim 1, wherein the blood treatment apparatus comprises:
a detection device in signal communication with the control device, the detection device configured to detect an established connection of a first component of the multiple components of the blood tubing set to the blood treatment apparatus,
wherein the control device is configured to act on a second component of the multiple components of the blood tubing set by the multiple devices of the receiving section, until detecting the established connection of the first component, and
wherein the first component and the second component are predetermined by the control device.

7. The blood treatment apparatus according to claim 1, wherein the blood treatment apparatus further comprises:
a detection device in signal communication with the control device and configured to detect an established connection to the blood treatment apparatus of a pre-determined first component of the multiple components of the blood tubing set;
wherein the control device is configured to:
request to connect the blood treatment apparatus to a pre-determined component of the organizer, via the user interface;
evaluate signals from the detection device regarding a detection of the established connection of the pre-determined first component; and
request to connect the blood treatment apparatus to a further pre-determined component of the organizer until the detection of an established connection of the pre-determined first component, and to act on the further pre-determined component by the multiple devices of the receiving section.

8. The blood treatment apparatus according to claim 1, wherein the blood treatment apparatus further comprises:
a detection device, in signal communication with the control device and configured to detect an established connection with the blood treatment apparatus of a device required for a blood treatment, or configured to detect the completion of a pre-determined action required for the blood treatment;
wherein the control device is configured to:
evaluate signals of the detection device regarding detecting the established connection of the device or the completed pre-determined action; and
act on a pre-determined component of the organizer by activating a device of the multiple devices of the receiving section during or until a detection of: (i) the established connection of the device or (ii) the completed pre-determined action.

9. The blood treatment apparatus according to claim 1, further comprising the organizer releasably connected to the multiple components of the blood tubing set.

10. The blood treatment apparatus according to claim 1, wherein the blood treatment apparatus is a hemodialysis apparatus, hemodiafiltration apparatus, hemofiltration apparatus, or apheresis apparatus.

11. An organizer comprising:
a rear member; and
at least one fastening device arranged on the rear member such that at least one component can be releasably held to the organizer by the at least one fastening device;
wherein the organizer defines an opening through which a device for acting on components may be brought into contact with the at least one component or with the at least one fastening device,
wherein the at least one fastening device comprises a releasable adhesive, and
wherein the at least one fastening device comprises a connector which is connectable to the device for acting on components.

12. The organizer according to claim 11, wherein the fastening device comprises a magnetic element.

* * * * *